(12) United States Patent
Bozic

(10) Patent No.: US 9,649,576 B2
(45) Date of Patent: May 16, 2017

(54) GAS-LIQUID SEPARATOR

(71) Applicant: SANOFI-AVENTIS DEUTSCHLAND GMBH, Frankfurt am Main (DE)

(72) Inventor: Alexander Bozic, Einhausen (DE)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 161 days.

(21) Appl. No.: 14/414,740

(22) PCT Filed: Jul. 17, 2013

(86) PCT No.: PCT/EP2013/065067
§ 371 (c)(1),
(2) Date: Jan. 14, 2015

(87) PCT Pub. No.: WO2014/012962
PCT Pub. Date: Jan. 23, 2014

(65) Prior Publication Data
US 2015/0174508 A1     Jun. 25, 2015

(30) Foreign Application Priority Data

Jul. 18, 2012 (EP) .................................. 12176869

(51) Int. Cl.
*B01D 45/00* (2006.01)
*B01D 19/00* (2006.01)
(Continued)

(52) U.S. Cl.
CPC ......... *B01D 19/0042* (2013.01); *B01D 15/10* (2013.01); *B01D 19/0057* (2013.01);
(Continued)

(58) Field of Classification Search
CPC B01D 19/0042; B01D 15/10; B01D 19/0057; B01D 45/08; B01D 45/16;
(Continued)

(56) References Cited

U.S. PATENT DOCUMENTS

| 1,756,288 A | 4/1930 | Gray et al. |
| 2,732,033 A * | 1/1956 | Parks ..................... B01D 45/08 55/391 |

(Continued)

FOREIGN PATENT DOCUMENTS

| CN | 1446611 A | 10/2003 |
| DE | 3715157 | 11/1988 |

(Continued)

OTHER PUBLICATIONS

International Search Report for Int. App. No. PCT/EP2013/065067, completed Sep. 2, 2013.
(Continued)

*Primary Examiner* — Dung H Bui
(74) *Attorney, Agent, or Firm* — McDonnell Boehnen Hulbert & Berghoff LLP

(57) ABSTRACT

A gas-liquid separator is provided having a chamber extending in an axial direction (z) and having at least a flow chamber portion extending into a collecting chamber portion. A deflector is arranged in the flow chamber portion and the deflector has a deflector panel extending radially outwardly (r) and in axial direction (z) to form a narrowing flow channel between the deflector and a side wall of the chamber, wherein the deflector panel has a free edge. There is at least one gas outlet shielded by the deflector panel and being arranged axially offset from the free edge.

16 Claims, 8 Drawing Sheets

(51) Int. Cl.
*B01D 45/08* (2006.01)
*B01D 45/16* (2006.01)
*B01D 46/24* (2006.01)
*B01D 50/00* (2006.01)
*B01D 46/00* (2006.01)
*B01D 45/12* (2006.01)
*B01D 15/10* (2006.01)
*B04C 3/06* (2006.01)
*B04C 3/00* (2006.01)

(52) U.S. Cl.
CPC .............. *B01D 45/08* (2013.01); *B01D 45/12* (2013.01); *B01D 45/16* (2013.01); *B01D 46/0005* (2013.01); *B01D 46/2411* (2013.01); *B01D 50/002* (2013.01); *B04C 3/06* (2013.01); *B04C 2003/006* (2013.01)

(58) Field of Classification Search
CPC .............. B01D 46/2411; B01D 50/002; B01D 46/0005; B01D 45/12; B04C 3/06; B04C 2003/006
See application file for complete search history.

(56) References Cited

U.S. PATENT DOCUMENTS

| | | | |
|---|---|---|---|
| 2,952,330 A | 9/1960 | Winslow | |
| 3,490,209 A * | 1/1970 | De Groote | B01D 45/06 55/430 |
| 3,507,098 A * | 4/1970 | Veres | F16T 1/14 137/194 |
| 4,092,130 A * | 5/1978 | Wikdahl | B01D 45/12 55/345 |
| 4,270,934 A | 6/1981 | Widdowson et al. | |
| 4,311,494 A * | 1/1982 | Conner | B01D 45/16 55/394 |
| 4,600,413 A | 7/1986 | Sugden | |
| 6,315,813 B1 | 11/2001 | Morgan et al. | |
| 2006/0230714 A1* | 10/2006 | Oh | B01D 45/02 55/319 |
| 2007/0163442 A1 | 7/2007 | Saito et al. | |
| 2008/0010956 A1* | 1/2008 | Fogelman | B01D 11/0203 55/319 |
| 2009/0000258 A1 | 1/2009 | Carlsson et al. | |
| 2009/0242490 A1 | 10/2009 | Hopper | |
| 2010/0072121 A1* | 3/2010 | Maier | B01D 45/16 210/196 |
| 2011/0024124 A1 | 2/2011 | Brown et al. | |
| 2014/0217031 A1* | 8/2014 | Wang | B01D 15/24 210/656 |

FOREIGN PATENT DOCUMENTS

| | | |
|---|---|---|
| EP | 2463004 A1 | 6/2012 |
| JP | S54-102664 A | 8/1979 |
| JP | S56-010904 U | 1/1981 |
| JP | S61-132733 U | 8/1986 |
| JP | H01-61914 U | 4/1989 |
| JP | H01-305203 A | 12/1989 |
| JP | H07-1277 U | 1/1995 |
| JP | H07-146035 A | 6/1995 |
| JP | 2001-054711 A | 2/2001 |

OTHER PUBLICATIONS

European Search Report for EP Application No. 12176869.1, dated Oct. 9, 2012.
International Search Report and Written Opinion for Int. App. No. PCT/EP2013/065067, mailed Sep. 11, 2013.

* cited by examiner

A-A

B-B

C-C

D-D

E-E

F-F

G-G

GAS-LIQUID SEPARATOR

CROSS REFERENCE TO RELATED APPLICATIONS

The present application is a U.S. National Phase Application pursuant to 35 U.S.C. §371 of International Application No. PCT/EP2013/065067 filed Jul. 17, 2013, which claims priority to European Patent Application No. 12176869.1 filed Jul. 18, 2012. The entire disclosure contents of these applications are herewith incorporated by reference into the present application.

TECHNICAL FIELD

The present invention relates to the field of gas-liquid separation. In particular, the invention focuses on gas-liquid separation for chromatography applications, in particular for separation of solvent mixtures used in high-performance liquid chromatography (HPLC), especially in super critical fluid chromatography (SFC). In an aspect, the invention relates to the separation of carbon dioxide ($CO_2$) and a co-solvent, such as ethanol or methanol.

BACKGROUND

Super critical fluid chromatography allows to separate a component, i.e. an extractant from another component, i.e. a matrix, by making use of a super critical fluid as the extracting solvent. By means of SFC and HPLC, various substances can be chemically analyzed, identified and quantified. Making use of carbon dioxide as a super critical fluid in SFC applications, the extraction of the substances has to be conducted under super critical conditions. Regarding carbon dioxide as the super critical fluid of choice, the extraction has to be conducted above the critical temperature of 31° C. and above a critical pressure of 74 bar.

For keeping $CO_2$ or a $CO_2$-mixture in a liquid state inside a chromatography column, the entire chromatography system has to be kept on a predefined pressure level. For this purpose, downstream of the chromatography column and downstream of a respective detector, a back-pressure regulator is typically provided, to keep the pressure inside the chromatography system on a predefined level.

In practical applications, SFC-technology comes along with the disadvantage, that a mobile phase of chromatographically separated substances cannot be easily collected in opened vessels. As soon as a mixture of liquid $CO_2$ and an additional solvent is exposed to atmospheric pressure, $CO_2$ abruptly expands and forms an aerosol with the additional solvent. A loss-less collection of the solvent requires sufficient gas-liquid separation of the aerosol.

Gas-liquid mixtures can be generally separated into a gaseous and into a liquid component by making use of inertia separators which operate according to the cyclone principle. There, an aerosol is tangentially inserted into a cone-shaped vessel. The aerosol propagates on a circular path so that its liquid particles drift radially outwardly until they impinge on the sidewall of said vessel. Due to their reduced mass, gaseous components experience less inertia force and may leave the cone-shaped vessel by means of a central immersion tube.

In SFC, the composition of the aerosol may strongly vary. The mixture of $CO_2$ and an additional solvent, such like methanol may vary from 10% to 60% methanol fraction. As a consequence, the constitution of the aerosol and its volume flow may vary accordingly thus leading to sub-optimal rates of separation of gaseous and liquid fractions of the aerosol in a cyclone-type separator.

Other gas-liquid separation systems for instance make use of impact separation, wherein the volume flow of the aerosol is directed onto a deflector plate, which may be even provided by a test tube.

In general, impact separators and inertia separators require a comparatively large volume into which the aerosol should expand. Such comparatively large vessels are not optimal in terms of self-cleaning effects and may therefore provide cross contamination of aerosols and substances being sequentially processed by such separators.

In principle, the size and the surface of impact separators can be minimized when operating at a raised pressure level. For instance, a test tube serving as a deflector plate can be provided in a pressurized environment. The aerosol may then escape from a bent outlet and may impinge on the sidewall of the test tube at a predefined angle. With such an impact separator it is indeed possible to collect smaller amounts of a substance at a much lower degree of cross contamination. But impact separators operating at a raised pressure level do not allow to realize a large scaled automated fractionation.

Hence, operating expenses and costs are comparatively high since only a limited amount of test tubes can be automatically processed in the pressurized area. Moreover, the rate of separation is not as good as with impact separators operating at atmospheric pressure.

It is therefore an object of the present invention to provide an improved gas-liquid separator featuring an improved rate of separation of gaseous and liquid components of an aerosol. The gas-liquid separator should further provide a high rate of separation even when the constitution and composition of the aerosol changes. Moreover, the gas-liquid separator should provide efficient separation of $CO_2$ and a solvent, like methanol, especially for SFC-applications. It is a further object of the invention to provide gas-liquid separation, which allows to realize a large-scaled automated fractionation and fraction collection for SFC, preferably at atmospheric pressure.

SUMMARY

In a first aspect a gas-liquid separator is provided, comprising a chamber extending in an axial or longitudinal direction (z). The chamber has at least a flow chamber portion and a collecting chamber portion. The flow chamber portion extends into the collecting chamber portion. Flow chamber portion and collecting chamber portion are therefore in flow communication with respect to each other. The gas-liquid separator further comprises a deflector, which is arranged in the flow chamber portion of the chamber. The deflector has a deflector panel extending radially outwardly and in axial direction (z) to form a narrowing flow channel between the deflector and a sidewall of the chamber.

The flow channel is provided between the deflector panel and the sidewall of the chamber, typically between the flow channel and a sidewall of the flow chamber portion. Due to the shape and orientation of the deflector panel, the cross section through which an aerosol or a gas-liquid mixture may flow decreases in transverse direction with respect to the direction of flow. As a consequence the diameter and size of the flow channel decreases in downstream direction.

Additionally, the deflector panel has a free edge, in particular a lower free edge.

In the present context a lower-, bottom- or distal portion refers to portions of the gas-liquid separator near or towards a downstream end whereas upper or proximal areas refer to upstream-located or upstream directed portions of the gas-liquid separator.

Consequently, the lower free edge is located at a distal end of the deflector panel facing towards the downstream direction of the gas-liquid separator.

The free edge of the deflector panel is located at a predefined distance to the surrounding sidewall of the chamber. The free edge then characterizes the smallest portion of the flow channel and provides a kind of a bottleneck.

The gas-liquid separator further comprises at least one gas outlet through which a gaseous component of an aerosol may leave the gas-liquid separator. The at least one gas outlet is shielded by the deflector panel and is further arranged axially offset from the free edge thereof. Typically, the at least one gas outlet is arranged at an axial distance from the lower free edge. Compared to an axial position of the lower free edge, the at least one gas outlet is displaced in proximal direction.

It is positioned in an area shielded by the deflector panel and is arranged in an axial position or area in which also the flow channel extends. The at least one gas outlet is arranged radially offset from the narrowing flow channel, typically in proximal or upstream direction. It is typically separated from said flow channel by the deflector panel. Hence, said deflector panel comprises a substantially closed surface or structure and is free of any through openings, orifices or slits.

By providing a deflector extending radially outwardly in axial and distal direction, the flow channel through which the provided aerosol has to flow narrows, thereby inducing an increase of the axially directed flow velocity of the aerosol. By providing the at least one gas outlet at a proximal distance from the lower free edge of the deflector panel, the gaseous component of the aerosol flows around the lower free edge and turns its direction of flow.

In order to reach the at least one gas outlet, the gaseous component of the aerosol may have to turn around the free edge by almost 180°. Since the aerosol experiences an axially and distally directed acceleration when flowing through the radially narrowing flow channel, the momentum and kinetic energy of liquid components of the aerosol may be too large and may therefore hinder its liquid components to follow the reversing and proximally directed motion of the gaseous components. In effect, after having passed the deflector panel and the narrowing flow channel, the liquid component of the aerosol may impinge the sidewall of the chamber and may be collected at a bottom or distal portion of said chamber, where the liquid is collected and guided to a liquid outlet.

The deflector panel may further axially divide the chamber of the gas-liquid separator into the flow chamber portion and into the downstream collecting chamber portion. The flow chamber portion may coincide with the narrowing flow channel formed by the deflector panel and the sidewall of the chamber. At the free edge of the deflector panel, the flow chamber merges into the collecting chamber portion. Compared to the narrowing flow channel, the collecting chamber portion abruptly provides an increased cross section into which the aerosol may expand. This sudden increase in cross section supports a deceleration of the gaseous component of the aerosol, whereas the liquid components, due to their larger mass and inertia may impinge on the sidewall of the chamber rather undamped.

In a further embodiment, the deflector panel is substantially cone shaped. It may completely surround the at least one gas outlet and may also provide a radially symmetric narrowing flow channel between the deflector and the chamber's sidewall. The angle at which the deflector panel extends with respect to the axial direction (z) may depend on the type of aerosol to be separated by the gas-liquid separator. Moreover, the angle and overall geometry of the deflector panel and the deflector may vary according to the geometric dimensions and geometric shape of the chamber.

The deflector panel may comprise a rather straight cone shape, such that the radial width of the narrowing flow channel constantly decreases in axial direction, in particular in distal direction.

However, it is also conceivable that the shape of the deflector panel deviates from a cone shape. At least in sections the deflector panel may comprise a curved or bended shape in a plane defined by the axial direction (z) and by a radial direction (r). Accordingly, the deflector panel at least in sections may comprise a convex or concave shaped geometry. Typically, the deflector panel comprises a radial and/or circumferential symmetry.

According to another embodiment the deflector panel comprises a radially-outwardly extending widening portion and a cylindrical portion. The cylindrical portion extends in axial direction. Furthermore, the cylindrical portion is arranged axially adjacent to the widening portion. As seen in a downstream direction, hence from a proximal or inlet end of the chamber towards a distal end, hence to a liquid collecting end, the deflector panel radially outwardly widens and extends into a cylindrical portion typically comprising an axial extension larger than the axial extension of the widening portion. In typical embodiments, the cylindrical portion extends more than 50%, more than 75%, more than 80% or even more than 90% of the total elongation of the deflector panel. Moreover, the cylindrical portion features a substantially constant diameter and shape in longitudinal, hence in axial direction.

The cylindrical portion forms an annular but longitudinally extending flow gap or a respective flow channel. The radial width of the flow gap or of the respective flow channel is much smaller than the inner diameter of the chamber. Typically, the radial size of the annular flow gap or of the annular flow channel is in the range of only a few millimeters or even below 1 mm.

The comparatively large axial extension of the deflector panel, in particular of its cylindrical portion may support inertia-based separation of gaseous and liquid components of the aerosol. A comparatively long cylindrical portion and a respective annular flow channel may provide and support generation of a well-defined axial flow behavior of the aerosol towards the free edge. In effect, an improved gas liquid separation can be attained.

In various embodiments the chamber of the gas-liquid separator comprises a cylindrical or tubular geometry. The sidewall of the chamber may comprise a cylindrical tube extending from an inlet chamber portion along a flow chamber portion and to a collecting chamber portion. The various chamber portions of the chamber of the gas-liquid separator may mutually merge in axial direction (z). In radial direction (r), the various chamber portions may be enclosed by a single and common tubular chamber.

In another embodiment, the free edge of the deflector panel forms an annular flow gap with the sidewall of the cylindrically shaped chamber. Typically, the free edge of the deflector panel is arranged at a predefined radial distance from the sidewall of the chamber. The free edge, which is provided as a lower end of the cone-shaped deflector panel comprises a circular structure and since the deflector and its deflector panel is oriented in axial direction and may be co-aligned with the longitudinal axis of the chamber, an annular flow gap between the deflector panel and the sidewall can be provided featuring a gap size, which is substantially constant in circumferential or tangential direction. Consequently, the deflector panel, in particular the cone-shaped deflector panel and the chamber with its flow chamber portion comprise mutually corresponding geometries and shapes being substantially invariant to rotations with the central longitudinal axis as axis of rotation. In embodiments wherein the annular flow gap is formed by a cylindrical portion of the deflector panel, the gap size is constant in radial and axial direction.

In a further embodiment the at least one gas outlet is in flow connection with an axially extending gas outlet duct. The gas outlet duct is typically arranged in a central portion of the chamber and may even coincide with its longitudinal axis. By means of the gas outlet duct, gaseous components entering the gas outlet can be discharged from the gas-liquid separator. A gas outlet duct may either extend in proximal or in distal direction and may further pass through a proximal- or distal-, hence, through an upper or a lower end portion of the chamber.

In a further aspect, the deflector comprises a closed base portion integrally formed with a proximal portion of the deflector panel to form a cup-shaped deflector. Consequently, once a gaseous component enters the deflector via the free edge, it may only escape from the interior of the deflector via the gas outlet. In various embodiments, the at least one gas outlet is arranged in close proximity to the base portion of the deflector. Typically, the gas outlet is arranged in an upper quarter or in an upper third of the axial elongation of the deflector. The at least one gas outlet is arranged closer to the base portion of the deflector than to its free edge. This way, the gas outlet can be effectively shielded by the deflector panel in order to effectively prevent that liquid components of the aerosol enter the gas outlet.

In another aspect, the deflector is arranged on a proximal end portion of the gas outlet duct. Moreover, the deflector may also be mounted on the gas outlet duct. The gas outlet duct may therefore serve as a mechanical support for the deflector. The radial dimensions or the diameter of the gas outlet duct may be at least slightly smaller than the radial or transverse cross section of the deflector's base portion. Moreover, the at least one gas outlet may be provided at a radially outwardly facing sidewall of the gas outlet duct and may face a substantially radially inwardly facing side wall portion of the deflector panel. The proximal end portion of the gas outlet duct may be provided with a plurality of radially directed gas outlets. The gas outlets may each comprise one or several through openings or may comprise the shape of an annular outlet slit provided in a proximal end portion of the gas outlet duct.

In various embodiments, a radial distance between the at least one gas outlet and an inward facing portion of the deflector panel is chosen such that the gas entering the radially extending gas outlet closely passes said portion of the deflector panel, such that further liquid components may precipitate even at the inward facing side wall portion of the deflector panel. When the gas-liquid separator is oriented with its proximal end in an upward direction, respective liquid components may rinse down the deflector panel and may drip down into the collecting chamber when reaching its free edge.

In another aspect, the gas-liquid separator further comprises a liquid collecting portion at a distal end section being in fluid connection with a fluid outlet duct. Typically, the liquid collecting portion is provided at a distal end of the collecting chamber portion. The liquid collection portion may provide a bottom section of the gas-liquid separator and may comprise a radially inwardly bevelled or slanted collecting surface, such that liquid components rinsing down the sidewall of the chamber accumulate in a radial central sink or depression from which the collected liquid can be discharged via the outlet duct.

In a further embodiment, the gas-liquid separator comprises a partition member, which is arranged upstream of the deflector and which extends over the cross-section of the chamber. The partition member serves to separate the flow chamber portion from an inlet chamber portion arranged upstream thereof. Generally, the aerosol provided to the chamber enters the chamber from the top or from a proximal end into the inlet chamber portion. Then, the aerosol has to pass the partition member in order to enter the flow chamber portion before entering the collecting chamber portion provided at a lower or distal end of the chamber of the gas-liquid separator.

In the inlet chamber portion, at least a pre-separation of liquid and gaseous components of the aerosol can be provided. In subsequent chamber portions, hence, in the flow chamber portion and/or in the collecting chamber portion, an additional and sequential gas-liquid separation can be conducted.

The partition member serves to control an inflow of gaseous and liquid components of the provided aerosol into the flow chamber portion. It may provide a throttle-effect. It may further induce, support or amplify a twisting motion of the aerosol and its components in circumferential or tangential direction (w).

In a further embodiment, the partition member comprises at least one axial through opening at an outer radial edge to form an axial passage through the partition member. The through opening is positioned adjacent to the sidewall of the chamber. The partition member may comprise a plurality of axial through openings, which are all provided at the outer radial edge thereof and which may be equidistantly arranged. This way, the partition member separates the inlet chamber portion and the flow chamber portion of the gas-liquid separator and provides a flow connection there between only via axial passages or through openings disposed near or at an outer radial edge thereof.

This way, the aerosol entering the inlet chamber portion is forced to flow through radially outwardly arranged through openings of the partition member, thereby directing the entire flow into the radial outer periphery of the chamber. An entry of the narrowing flow channel corresponds with the size and position of the at least one axial through opening of the partition member. This way, once the aerosol has passed the at least one axial through opening of the partition member it directly impinges the narrowing flow channel provided in the flow chamber portion downstream thereof.

In still another embodiment, the at least one through opening of the partition member extends at a predefined angle with respect to the axial direction (z). When a plurality of axial through openings is provided, the through openings or channels formed by these through openings may all extend parallel at the same predefined angle with regard to the axial direction (z). The axial dimensions of the through openings may vary according with the axial thickness of the partition member.

As already mentioned, the at least one axial through opening may comprise a channel-like geometry, which may extend at a certain angle with respect to the axial direction. This way, the through opening or the channel formed by such through opening may provide a somewhat skewed orientation and may induce a twisting or vortex-like motion on the aerosol and its components. Depending on the shape and angle the at least one through opening of the partition member extends, a swirling motion of the aerosol extending there through may be varied accordingly.

The angle and the axial extension of the at least one through opening of the partition member may be chosen such that a laminar-dominated flow of a liquid component of the aerosol rinses down along the side wall of the chamber.

In a further embodiment the gas-liquid separator also comprises an inlet duct, which extends into the chamber in axial direction. The inlet duct may extend through a proximal end of the gas-liquid separator, typically through a head section, which serves as a proximal lid of the gas-liquid separator. The inlet duct may be arranged in a radial centre of the chamber and serves to spread and/or to distribute the aerosol radially outwardly into the inlet chamber portion. Consequently, the inlet duct is radially centrally arranged inside the chamber and is further in fluid connection with at least one inlet facing radially outwardly towards the sidewall of the chamber.

In embodiments without a partition member the inlet chamber portion is substantially equivalent to the flow chamber portion and vice versa. Here, the inlet duct may represent a cylindrical portion the of the flow chamber adjacent to an upper section of head section of the chamber, while the flow chamber portion comprises a cross section for the incoming aerosol that varies or narrows in axial distal direction.

By providing a plurality of inlets all being in fluid connection with the inlet duct, the aerosol can be distributed in the inlet chamber portion radially outwardly towards the sidewall of the chamber and its respective inlet chamber portion. By way of directing the aerosol from a radial central area radially outwardly towards the sidewall of the chamber, an impact-based pre-separation of the aerosol can be provided in the inlet chamber portion.

In a further aspect the inlet duct branches off into a plurality of radially extending inlets at a proximal end of the chamber. The inlet or the plurality of inlets is typically arranged at a predefined axial distance from the partition member. The inlets may not only extend strictly in radial direction but may point also in tangential or axial direction for directing the incoming aerosol accordingly.

While the gaseous components may easily re-distribute and flow towards the axial through openings of the partition member, the liquid components may impinge and precipitate on the sidewall of the inlet chamber portion. As a consequence, the pre-separated liquid components may rinse down along the sidewall of the chamber through the axial through openings of the partition member and into the flow chamber portion. There, the stream of the residual aerosol is accelerated in axial distal direction, typically in such a way, that a substantially laminar flow of the liquid component along the chamber's sidewall is not torn apart.

In a further embodiment, the at least one inlet comprises a curved section extending into the inlet chamber portion or extending into the flow chamber portion. Said curved section faces in a proximal direction with a free end. Typically, the free end of the inlet, from which the aerosol is fed into the inlet chamber portion and/or flow chamber portion points upwardly, e.g. towards an inward and downward oriented face of a head section of the chamber of the gas liquid separator.

Typically, the curved inlet may radially-outwardly protrude from a base portion of the deflector and may hence radially-outwardly protrude into the inlet chamber portion or into a respective flow chamber portion. Since its free end faces in axial direction, typically opposite to the supply direction of the aerosol entering the inlet, the aerosol becomes subject to an inertia-based as well as to an impact-based separation when redirected by the curved section of the at least one inlet. With such an embodiment the shape and geometry of the inlet supports and provides improved gas liquid separation.

The pre-separated liquid component obtained by the impact-based separation, which may take place in the inlet chamber portion as well as in the flow chamber portion, rinses down the entire side wall of the chamber until it is collected or accumulated by the liquid collecting portion at the distal end section of the gas-liquid separator.

Residual liquid components may enter the flow chamber portion together with the gaseous component and may experience an axially directed acceleration when flowing through the narrowing or narrowed flow channel. The narrowing or narrowed flow channel together with the free edge of the deflector panel provides a subsequent inertia separator. Once a mixture of gaseous and liquid components has passed the lower free edge of the deflector panel, the gaseous components may easily turn around the free edge and may flow upwardly or proximally into the at least one gas outlet. Due to their comparatively large inertia, the liquid components may not be able to follow the axially turning stream of gaseous components and may therefore impinge or precipitate on the sidewall of the collecting chamber portion.

By providing an inlet duct and an outlet duct in a radial central area of a gas-liquid separator and by arranging the inlet duct and a gas outlet duct substantially parallel to each other in two axially separated chamber portions, a two-step and sequential gas-liquid separation can be provided. In a first step, the provided aerosol can be pre-separated by impact-based or impact-dominated separation taking place in the inlet chamber portion. Subsequently, an inertia-based or inertia-dominated separation of the residual aerosol can be provided by the particular shape and geometry of the deflector and the gas outlet being arranged axially offset from the free edge of the deflector panel.

Due to symmetry reasons the chamber may be of cylindrical shape. However, the sequential impact-based and inertia-based separation does not generally require a tangentially directed twisting motion of the provided aerosol. In contrast to conventional cyclone-type gas-liquid separators the inertia-based separation provided by the present deflector and the gas outlet provides rather high rates of separation even for a large variety of differently composed gas-liquid compositions. Moreover, the partition member may be mounted in the chamber by means of a holder being co-aligned with the inlet duct.

Apparently, the impact-base and inertia-based separation may also take place simultaneously in the flow or inlet chamber portion and in the collecting chamber portion, respectively. Typically the separation in the flow chamber portion may be dominated by impact separation while separation in the collecting chamber portion may be dominated by inertia-based separation.

The holder may comprise a rod-like shape and may extend from a head section of the gas-liquid separator in distal direction into the chamber. The holder may comprise a hollow rod, which may also receive the inlet duct and which may be perforated or intersected by a plurality of radially outwardly directed inlets.

By mounting the partition member on the holder, the gas-liquid separator may be easily assembled and disassembled, especially for cleaning or maintenance purpose. Hence, the head section together with the inlet duct, the holder and optionally with the partition member may be pre-assembled as a head module, whereas the gas outlet duct and the cup-shaped deflector mounted thereon could be pre-assembled with a bottom section of the gas-liquid separator thereby serving as a bottom module.

This way, the gas-liquid separator could also be re-configured by combining or replacing individual parts thereof. It is for instance conceivable that a bottom module consisting of a bottom section, the gas outlet duct and the deflector is disassembled and removed from the gas-liquid separator for exchanging the deflector. In a similar way, also a head module could be easily converted by replacing at least one of its components. Generally, by exchanging components of the gas-liquid separator, such like deflector and/or the partition member the gas-liquid separator could be easily re-configured. Consequently, the gas-liquid separator may be universally adapted to different types of gas-liquid mixtures or aerosols.

In a further independent aspect, the invention also relates to a chromatography system. Such system comprises at least one reservoir for storing and/or for preparing at least one solvent mixture. The chromatography system further comprises at least one chromatography column and at least one detection or analyzing unit for analyzing, identifying and quantifying substances. The chromatography system further comprises at least one gas-liquid separator as described above.

In a further aspect, the chromatography apparatus is designed as super critical fluid chromatography (SFC) apparatus, wherein the gas-liquid separator is operable to separate an aerosol, typically comprising $CO_2$ and methanol.

First experiments with such a gas-liquid separator have revealed a rate of separation above 98%, wherein the $CO_2$- component could be recaptured at a rate of 96% to 98%. The methanol component could be recaptured at a rate of 97% to 99%. These and even better rates of separation can be obtained with a large variety of different compositions of a $CO_2$-methanol mixture. The gas-liquid separator is therefore adapted to provide a large degree of separation even for varying concentrations of $CO_2$ and methanol in the aerosol.

Additionally, the gas-liquid separator requires only a minimum of space and comprises a comparatively small volume. Consequently, the gas-liquid separator inherently provides a beneficial self-cleaning effect, since almost any component of the gas-liquid separator is washed round by the aerosol and/or its liquid component. Hence, the diameter of the chamber may be as small as a view centimeters. Typically, the diameter of the chamber is smaller than 5 cm. It may be even smaller than 4 cm or the diameter may be around 3 cm or even less.

The gas-liquid separator may be generally operated at atmospheric pressure. However, in order to avoid accumulation of larger amounts of liquid, e.g. of methanol, the gas-liquid separator may be operated at a moderate internal back-pressure of, for instance 1.5 bar to be provided by a back-pressure regulator.

However, the liquid component collected via the collecting chamber portion and provided by the liquid outlet duct allows for an automated fractionation, which is operable under atmospheric pressure. By means of the gas-liquid separator and comparable to conventional HPLC-analysis a fully automated fraction collection can be implemented even for the SFC-analysis.

Since internal walls and components of the gas/liquid separator are substantially permanently moistened not only a self-cleaning effect may evolve but also a rather low degree of cross contamination of samples can be achieved. As a further benefit, the separator induces a rather low degree of peak broadening in resulting chromatograms.

In effect, the gas-liquid separator helps to reduce the complexity and costs of the technical equipment required to set up SFC-analysis.

According to another aspect also a conversion kit is provided that supports and allows to convert a high-performance liquid chromatography (HPLC)-type chromatography system into a SFC-type chromatography system. Hence, the conversion kit is operable and configured to convert a HPLC system into an SFC system. Such a kit comprises at least a gas liquid separator as described above, which is configured and adapted to replace another gas liquid separator of a typical HPLC-type chromatography system.

It will be further apparent to those skilled in the pertinent art that various modifications and variations can be made to the present invention without departing from the spirit and scope of the invention. Further, it is to be noted, that any reference signs used in the appended claims are not to be construed as limiting the scope of the present invention.

BRIEF DESCRIPTION OF THE DRAWINGS

In the following, various embodiments of the invention will be described by making reference to the drawings in which.

DETAILED DESCRIPTION

Figure 1:
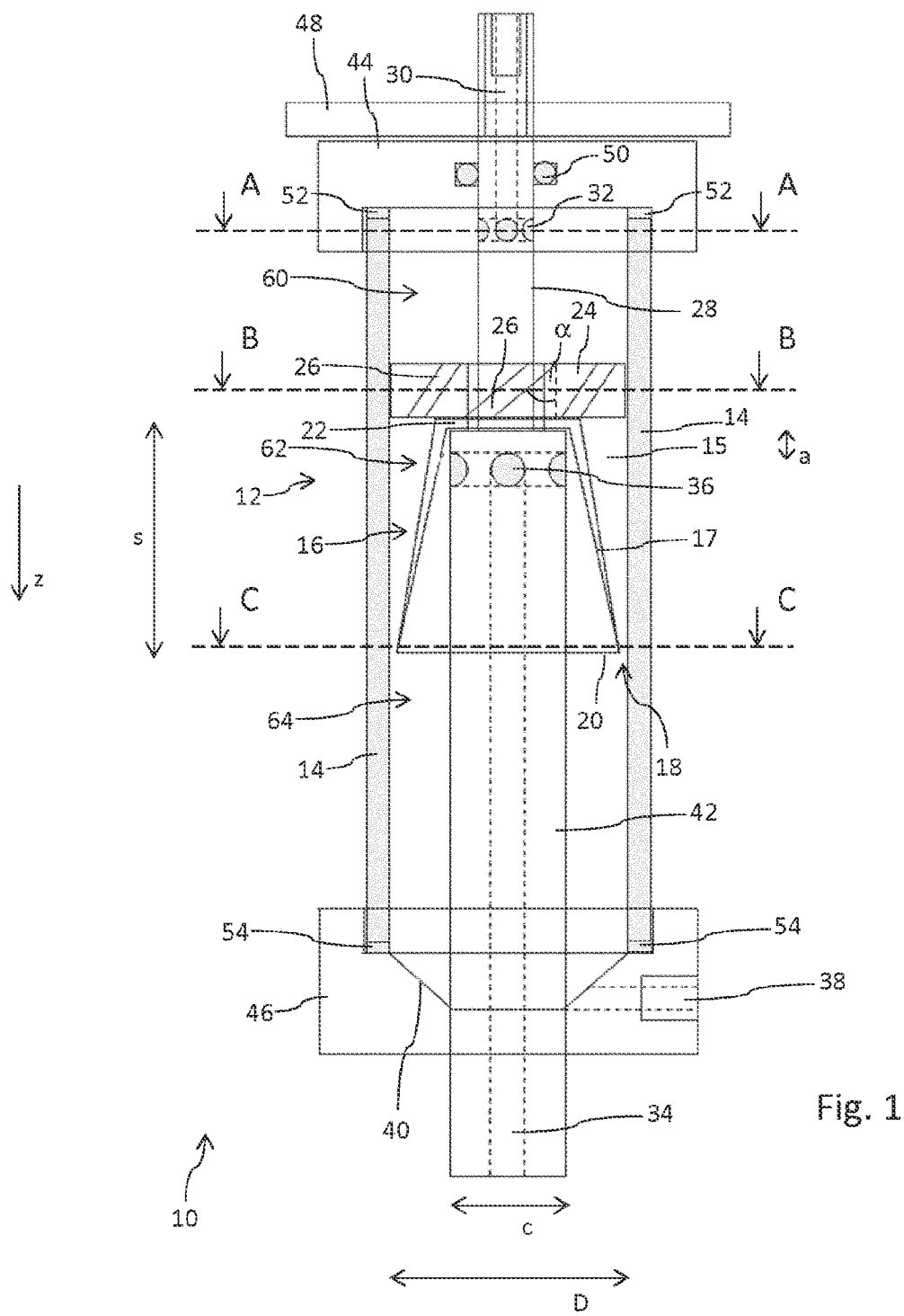
FIG. 1 schematically illustrates the gas-liquid separator in longitudinal cross-section.

In FIG. 1 the gas-liquid separator 10 is shown in a longitudinal cross-section. The gas-liquid separator 10 comprises a substantially cylindrical chamber 12 having a sidewall 14 and extending in axial direction (z). Towards an upper or proximal end, the chamber 12 is closed by means of a head section 44 having a lid 48, which may be provided as a knurled nut. The head section 44 receives the tubular-shaped chamber 12 and is sealed with regard to the chamber 12 with an annular seal 52.

The head section 44 is intersected by an inlet duct 30, which extends into a plurality of radially outwardly directed inlets 32. As shown in cross-section according to FIG. 2 the axially extending inlet duct 30 splits into four radially outwardly directed inlets 32 by way of which the provided aerosol can be spread against an inward facing portion of the side wall 14. As further shown in FIG. 1, a holder 28 intersects the head section 44 and a respective passage through the head section 44 is sealed by means of an annular seal 50.

Figure 2:
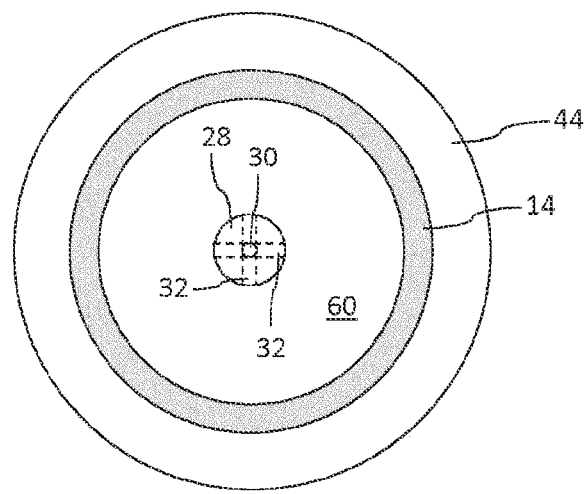
FIG. 2 shows a transverse cross-section of the gas-liquid separator according to FIG. 1 along A-A.
Figure 3:
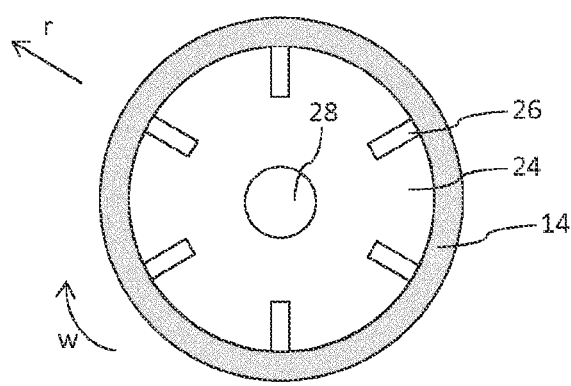
FIG. 3 shows a transverse cross-section of the gas-liquid separator according to FIG. 1 along B-B.
Figure 4:
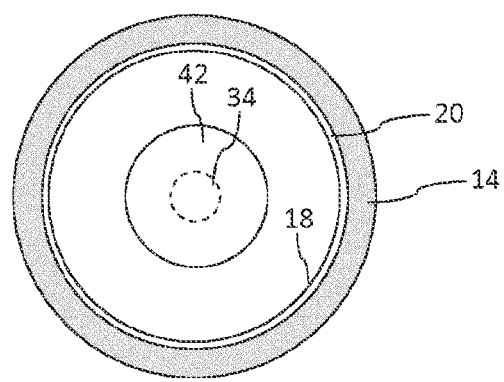
FIG. 4 shows a transverse cross-section of the gas-liquid separator according to FIG. 1 along C-C, FIG. 5 schematically illustrates a block diagram of an SFC-system making use of the gas-liquid separator as shown in FIGS. 1 to 4, FIG. 6 schematically illustrates another embodiment of the gas-liquid separator in longitudinal cross-section.
Figure 5:
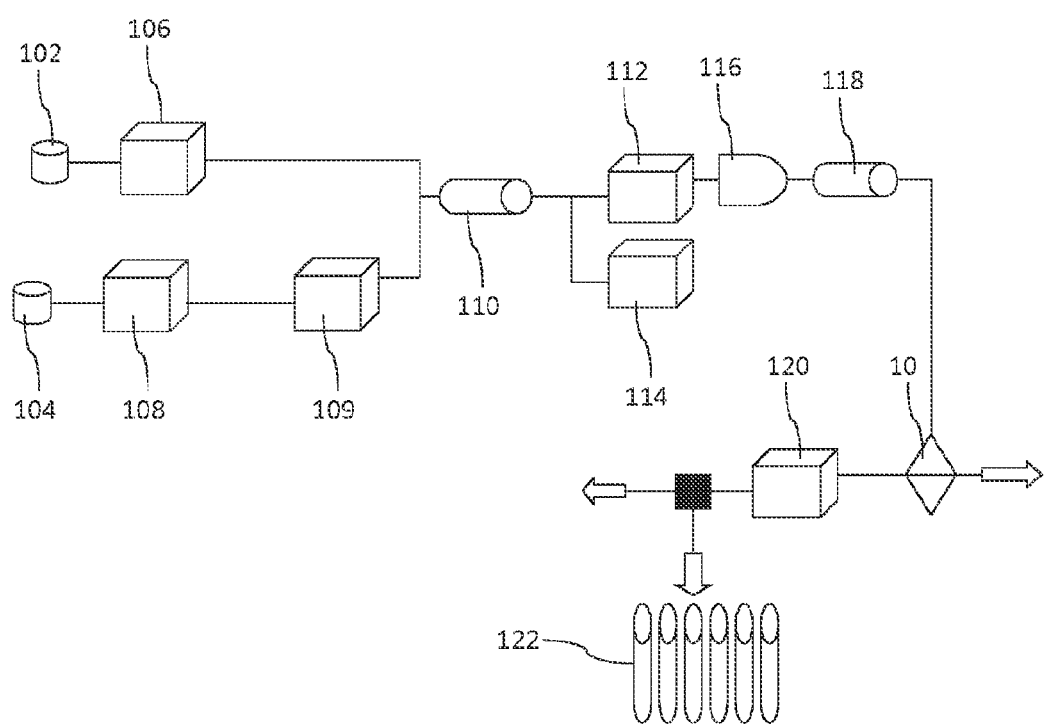

As further shown in FIGS. 1 and 2, the inlet duct 30 is arranged inside a tubular-shaped holder 28 extending in distal direction through an the inlet chamber portion 60. The holder 28 holds a disc-shaped partition member 24, which serves to separate the upper inlet chamber portion 60 from a flow chamber portion 62. The partition member 24 extends over the entire lateral cross-section of the chamber 12 and therefore serves as a throttle-element for the incoming aerosol.

In the inlet chamber portion, a pre-separation of the aerosol may take place. Since the inlets 32 extend through the holder 28, the provided aerosol can be directed radially outwardly towards the sidewall 14 of the chamber 12. There, the sidewall 14 serves as a kind of deflector plate and liquid components of the aerosol may precipitate at the sidewall 14. Since the gas-liquid separator 10 as shown in FIG. 1 is to be operated in the upright configuration as illustrated, liquid components accumulated at the side wall 14 of the inlet chamber portion 60 may rinse down in distal direction under the effect of gravity.

The partition member 24 as shown in cross-section in FIG. 3 comprises a plurality of axial through openings 26 provided at an outer radial edge thereof. These through openings 26 provide axial passages through the partition member 24 along the sidewall 14 of the chamber. As indicated in FIG. 1 the passages formed by the axial through openings 26 comprise a channel-like structure and may extend at a certain angle α with respect to the axial direction (z).

By means of such a slanted or skewed orientation of the passages, the aerosol, hence its gaseous and liquid components may experience circumferential, hence tangential (w), e.g. a clockwise twisting motion when entering the flow chamber 62 with regard to the general direction of a distally directed flow.

The skewed or slanted passages through the partition member 24 may induce a certain spin or twist to the liquid and gaseous components. Moreover, by means of the skewed passages 26 a flow of a liquid component downstream in the flow chamber section 62 can be homogenized and the respective liquid component may homogeneously distribute along the inner circumference of the sidewall 14. This way, a rather homogeneous liquid film may be provided along the inside facing surface of the sidewall 14 in the flow chamber portion 62.

Downstream of the inlet chamber portion 60 and downstream of the partition member 24 there is provided a flow chamber portion 62, in which a deflector 16 is arranged. As illustrated in FIG. 1, the deflector 16 comprises a substantially flat and even-shaped closed base portion 22 and a cone-shaped deflector panel 17, which extends distally in axial direction (z) and radially outwardly (r) towards the distal direction.

This way, a flow channel 15 formed between the sidewall 14 and the deflector panel 17 which constantly decreases in size towards the distal direction. As a consequence, the flow of liquid and gaseous components accelerates and traverses an annular gap 18 between a free edge 20 of the deflector panel 17 and the sidewall 14 with increased velocity. Acceleration of the mixed liquid and gaseous components provides a subsequent inertia-based separation of gaseous and liquid components of the aerosol.

As indicated in FIG. 1, a gas outlet 36 is arranged axially offset and proximally shifted from the free edge 20. By providing a suitable pressure gradient in a downstream gas outlet duct 34 compared to the collecting chamber 64, the gaseous components will be able to turn around and to flow radially inwardly and upwardly to enter the gas outlets 36 being in flow connection with the axially extending gas outlet duct 34. Due to an increased velocity and due to their inertia, most of the liquid components entering the collecting chamber 64 downstream of the free edge 20 will not be able to follow the upwardly turning flow of gaseous components. As a consequence, liquid components of the aerosol entering the collecting chamber 64 will further impinge and precipitate at the sidewall 14 of the collecting chamber portion 64.

In effect, the gas-liquid separator 10 provides a two-step gas-liquid separation. In a first step, impact-based separation takes place in the inlet chamber portion 60 and in a second step, inertia-based separation takes place in the collecting chamber 64 portion downstream of the flow chamber portion 62.

A bottom section 46 serves as a distal closure of the chamber 12 and is attached to the chamber 12 via another annular seal 54. Adjacent to a distal end of the cylindrically-shaped side wall 14 the bottom section 46 provides a bevelled collecting portion 40 by way of which liquid components rinsing down the side wall 14 can be collected in a radially central portion and can be provided to a liquid outlet duct 38.

As illustrated in FIG. 1, the gas outlet duct 34 extends in axial direction and co-aligns with a longitudinal or symmetry axis of the chamber 12. Furthermore, the gas outlet duct 34 axially intersects the collecting portion 40 and the bottom section 46.

Additionally, the gas outlet duct 34 is arranged inside a tubular-shaped holder 42, which serves as a mount for the deflector 16. As shown in FIG. 1, a downward directed and inward facing side of the base portion 22 of the deflector 16 rests on a proximal end of the holder 28. The radial extension of the base portion 22 substantially coincides with the radial width or with the diameter of the holder 28. As further shown in FIG. 1 several gas outlets 36 extend radially inwardly and merge into the gas outlet duct 34.

Here, the various gas outlets 36 may radially extend through the holder 28. They are provided at an axial distance (a) from the base portion 22 in order to provide enough free space to the inward facing side wall portion of the deflector panel 17. Depending on the geometric dimensions, in particular the radial and axial dimensions of the base portion 22, the deflector panel 17, the size of the annular gap 18 and the size and position of the various gas outlets 36, the flow conditions inside the chamber 12 and a corresponding rate of separation may vary.

When entering the collecting chamber portion 64 the gaseous components turn around in upward or proximal direction and enter the inner portion of the cup-shaped deflector 16. There, the stream of gaseous components is guided by the radially inwardly and upwardly extending deflector panel 17. Upon entering the gas outlet 36, the flow of gaseous components is re-directed radially inwardly, whereby the deflector panel 17 may serve as a deflector plate at which additional liquid components may precipitate. Accumulated liquid components may then rinse downward towards the free edge 20 and may drop down into the collecting chamber portion 64.

By mounting the partition member 24 on a proximal and axially extending holder and/or by mounting the deflector 16 on a comparative but distally located holder 42, various components of the gas-liquid separator 10, such like the partition member 24 and the deflector 16 could be easily assembled, disassembled and exchanged by corresponding but differently shaped components. Moreover, by mounting the deflector 16 on a central holder 42, the annular gap 18 can be kept interruption-free.

In a similar way, the arrangement of the partition member 24 inside the chamber 12 does not require any mutually corresponding fastening means. Moreover, by mounting the partition member 24 on a proximal holder 28 and by arranging the deflector 16 on a distal holder 42 respective proximal and distal modules or sub-assemblies can be provided. By modifying for instance the axial length of the proximal holder 28 and/or of the distal holder 42, the axial positions and the distance between the partition member 24 and the deflector 16 may be varied.

Consequently, also the size of the inlet chamber portion 60, the flow chamber portion 62 and the collecting chamber portion 64 may be modified accordingly. This way, the gas-liquid separator 10 can be tuned, adapted and configured to provide gas-liquid separation for a variety of different aerosols.

It is further to be noted that in typical embodiments, the axial length (s) of the deflector 16 is at least ⅓ of the diameter (D) of the chamber 12. The axial elongation (s) of the deflector 16 may be even comparable or be larger than the diameter (D) of the chamber 12. Furthermore, the diameter (c) of the base portion 22 of the deflector 16 may range between ⅓ to ¾ of the diameter (D) of the chamber 12. Typically, the diameter (c) of the base portion 22 is around ⅔ of the diameter (D) of the chamber 12.

The block diagram according to FIG. 5 schematically illustrates an implementation of the gas-liquid separator 10 in a super critical fluid chromatography system 100. Such system is exemplary illustrated by making use of super critical $CO_2$ in addition with methanol as a solvent. As shown in FIG. 5, $CO_2$ is provided in a storage tank 102 and methanol is provided in a storage tank 104. The $CO_2$ storage tank 102 is in fluid connection with a preparation stage 106. The preparation stage 106 may comprise a pump as well as a heat exchanger.

In a similar way, the methanol storage tank 104 is in flow connection with a corresponding preparation stage 108, which typically comprises a respective pump and a heat exchanger. Downstream of the preparation stage 108 there is typically provided a probe injector 109. The $CO_2$ component and the methanol component together with the probe is then mixed and provided to a chromatography column 110. Downstream of the chromatography column 110 there is provided at least one detection or analyzing unit 112, 114.

In the illustrated block diagram, a UV-detector 112 and a mass spectrometer 114 are provided. Downstream of the UV-detector 112 there is further provided a back-pressure regulator 116 and a heat exchanger 118. The aerosol leaving the heat exchanger 118 is provided to the gas-liquid separator 10 as described above. While the $CO_2$ component is released to the environment, the methanol component is collected in a fraction collector 120. The collected fractions can be automatically collected as main fractions 122 while excess methanol may become subject to disposal.

Another embodiment of a gas-liquid separator 130 is for instance illustrated in FIGS. 6 to 8. Unless otherwise indicated there, similar or like components of the gas-liquid separator as already described with FIGS. 1 and 2 are denoted with the same of like reference numerals. The general working principle and the flow of gaseous and liquid components is substantially unmodified. However, the geometry of the gas-liquid separator 130 of FIGS. 6 to 8 slightly changes from the embodiment as shown in FIGS. 1 and 2.

As indicated in FIG. 6, the deflector 16 and its deflector panel 17 comprises a larger extension in axial direction (z). Hence, the axial length (s) of the deflector 16 at least equals the inner diameter of the chamber 12. The axial length (s) may even be as large as twice the diameter of the chamber 12. This rather elongated deflector 16 serves to reduce the velocity of the gaseous component at its lower free edge 20. This supports a turning of the gaseous component and may therefore lead to higher separation efficiency.

Moreover, the gas outlets 36 are arranged in direct vicinity of the base portion 22 of the deflector 16. This way, an axial distance between the free edge 20 of the deflector panel 17 and the gas outlets 36 can be maximized, which further enhance separation efficiency.

As it is further apparent from FIG. 6, the gas-liquid separator 130 does no longer comprise a partition member 24. Consequently, the inlet chamber portion 60 and the flow chamber portion 62 directly merge. As a consequence, the deflector 16 with its upper base portion 22 directly and axially abuts with the head section 44. Additionally, the entire chamber 12 may be encapsulated by a transparent protection assembly 134.

Since the embodiment according to FIGS. 6 to 8 does no longer comprise a partition member 24 a twisting or swirling motion of the provided aerosol can be induced by tangentially and radially outwardly extending inlets 132 as shown in cross-section in FIG. 6. These tangentially extending inlets 132 are arranged and provided in the base portion 22 of the deflector 16.

By omitting the partition member 24 perturbations of the flow of the aerosol can be substantially reduced or almost entirely eliminated. There might evolve a laminar governed flow along the inside portion of the side wall 14.

Further and in contrast to the embodiment of FIGS. 1 and 2, the base portion 22 of the deflector 16 is axially enlarged to receive the inlet duct 30. As becomes apparent from FIG. 8, the gas-liquid separator 130 comprises an axially extending insert 140 extending through the chamber 12 and through the gas-liquid separator 130. The insert 140 provides the inlet duct 30 at an upper end and the holder 42 with the gas outlet duct 34 at a lower end portion.

As further indicated in FIG. 8, these upper and lower portions 30, 34 are hermetically separated by an intermediate portion 142 provided there between and having an annular recess 144 at a radially outwardly facing side wall portion to receive a seal 50. This intermediate portion 142 is particularly adapted to engage with a bore of the base portion 20 of the deflector 16. In this way, the deflector 16 can be simply mounted on the insert 140.

Deflector 16 and insert 140 are mutually arranged such that the tangentially and radially outwardly extending inlets 132 of the deflector 16 substantially align and flush with the radially outwardly extending inlets 32 of the inlet duct 30.

First experiments with the gas-liquid separator 130 have shown that the dynamic range of the gas-liquid separation can be further extended. In effect, such gas-liquid separators 10, 130 may even be operable at a methanol fraction of larger than 65%, even larger than 75% or even at methanol fractions of up to 85%.

Figure 6:
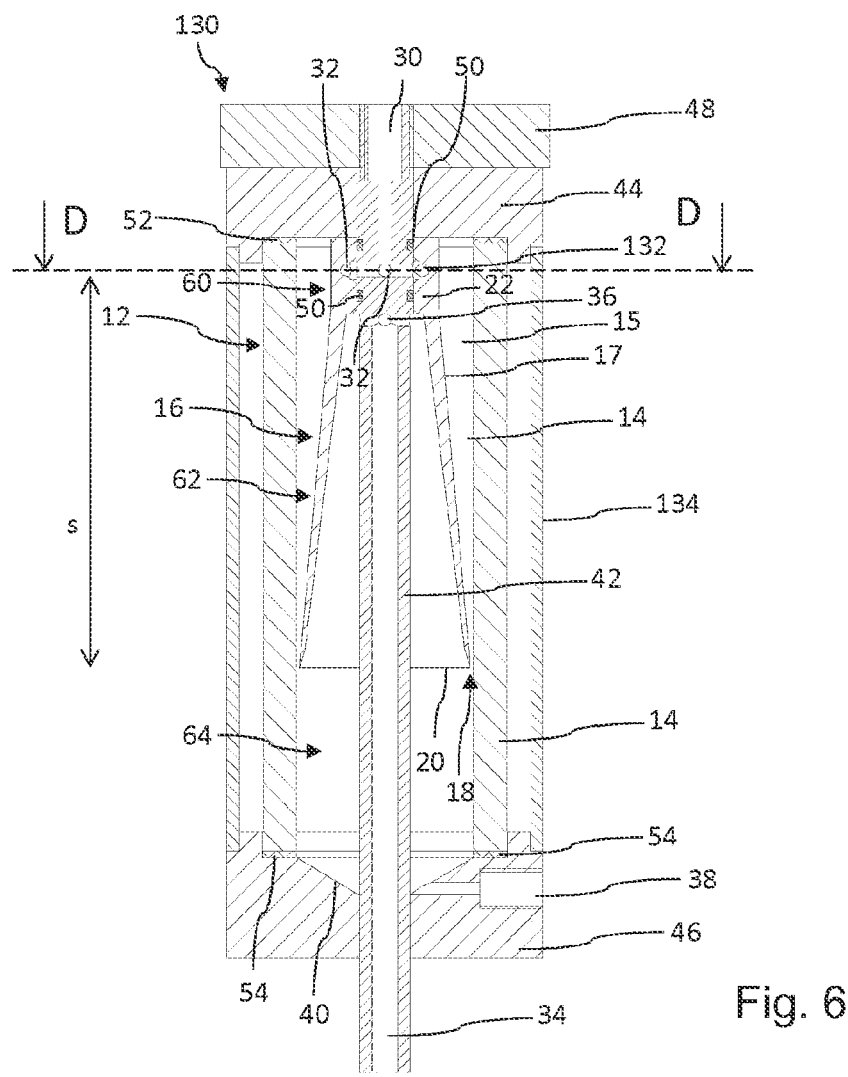
Figure 7:
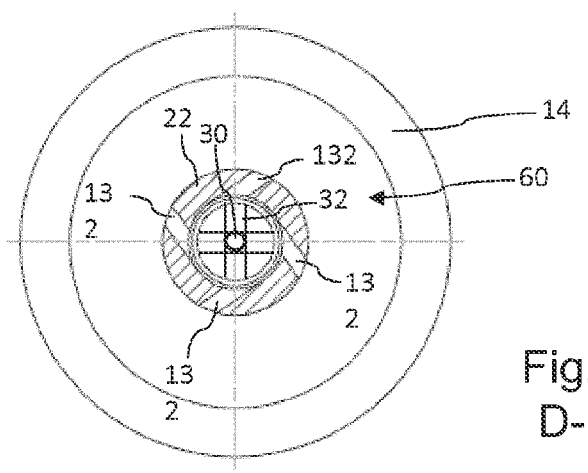
FIG. 7 shows a cross-section of the gas-liquid separator according to FIG. 6 along D-D.
Figure 9:
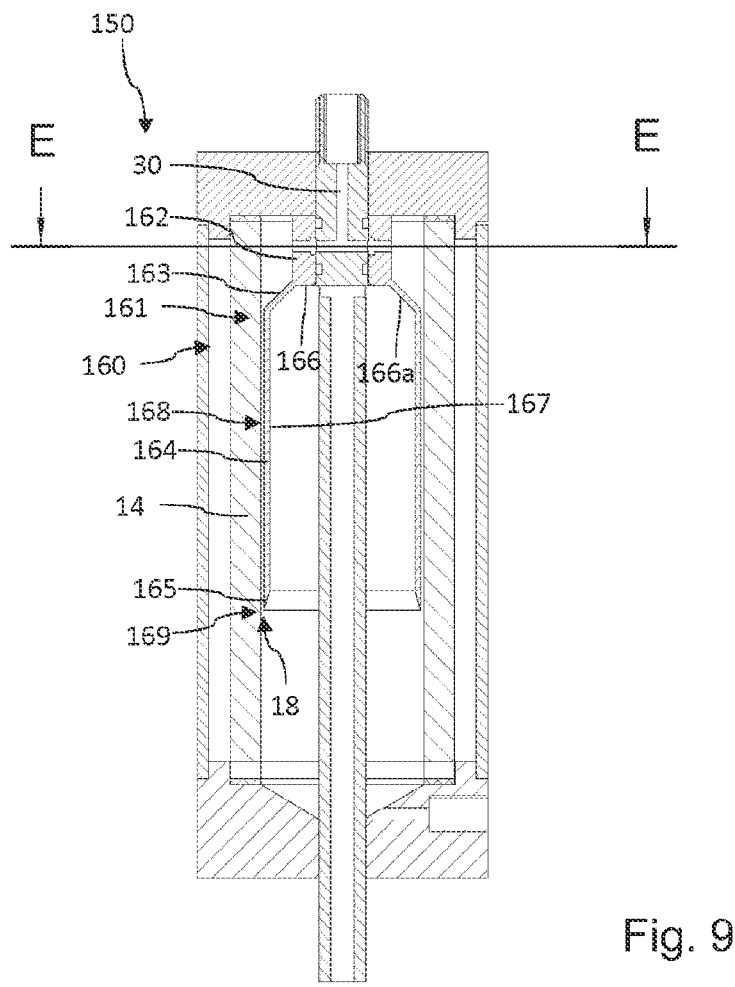
FIG. 9 shows a longitudinal cross section of another embodiment of the gas liquid separator.
Figure 10:
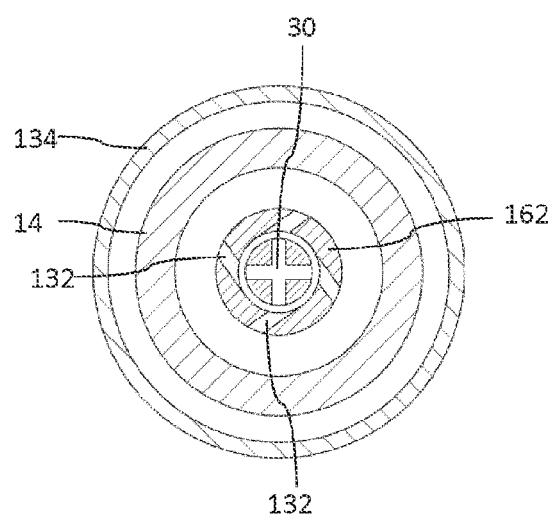
FIG. 10 shows a cross-section of the gas liquid separator according to FIG. 9 along E-E.

In FIGS. 9 and 10 another gas liquid separator 150 is illustrated exhibiting a large degree of similarity to the embodiment according to FIG. 6. Unless not further indicated, similar or like components of the gas liquid separator as described in FIGS. 6 and 7 are denoted with the same or like reference numerals. The gas liquid separator 150 according to FIG. 9 varies from the embodiment according to FIG. 6 by the geometric shape of the deflector 160. The deflector 160 of the gas liquid separator 150 comprises a deflector panel 161 and a base portion 162.

Figure 8:
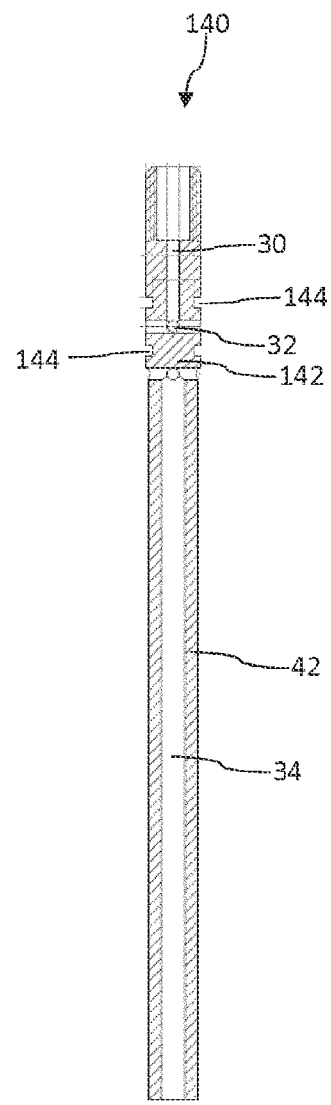
FIG. 8 shows a longitudinal cross section of an insert arranged in the gas-liquid separator of FIGS. 6 and 7.

The base portion 162 is of substantially sleeve-like or cylindrical shape and is fitted onto the intermediate portion 142 of the insert 140 as separately illustrated in FIG. 8. From a lower end, hence from a distal end of the base portion 162 there extends a radially widening portion 163. The radially outwardly widening portion 163 is of cone shape and comprises a rather planar but beveled outer surface. At its lower end, hence at its radially widened end, the widening portion 163 extends into a cylindrical portion 164. As illustrated in FIG. 9, the cylindrical portion 164 is of substantially sleeve-like geometry and is aligned coaxial with the sidewall 14 of the chamber 12.

Between the axially elongated cylindrical portion 164 and the sidewall 14 there extends an annular flow channel 168 that terminates in an annular flow gap 18 at the free edge 169 of the deflector panel 161. The free edge 169 is located at the free end of the cylindrical portion 164 of the deflector panel 161. The free edge 169 is particularly characterized by a beveled or tapered sidewall portion 165. Said tapered sidewall portion faces radially inwardly so that the annular flow channel 168 and hence the annular flow gap 18 remains substantially unaffected by said tapered sidewall portion 165.

The axial extension of the cylindrical portion 164 may be 2-15 times larger than the axial extension of the radially widening portion 163 of the deflector panel 161. Typically, the axial extension of the cylindrical portion 164 is about 8-12 times larger than the axial extension of the radially widening portion 163. Moreover, the deflector panel may be formed from a single piece. Hence, base portion 162, radially widening portion 163 and the cylindrical portion 164 may be integrally formed.

As it is illustrated in FIG. 10, the inlet duct 30 is rather similar or almost identical to the inlet duct of the gas liquid separator 130 as illustrated in FIGS. 6 and 7. Also here, the axially extending and substantially centrally located inlet 30 branches off into four radially outwardly and/or radially outwardly and tangentially extending inlets 132. The inlets 132 are provided in the base portion 162 of the deflector 160. As already described in regard to the embodiment according to FIGS. 6-8, the radially and/or tangentially outwardly extending inlets 132 of the deflector 161 substantially align and flush with the radially-outwardly extending inlets 32 of the inlet duct 30.

The outer geometry of the deflector panel 161 also reflects at its radially-inwardly-facing inside wall section 167. Apart from the tapered end 165, the inside wall section 167 is also of substantially cylindrical geometry. This is not only valid for the cylindrical portion 164 but also for the radially widened portion 163.

Hence, the deflector panel 161 comprises a rather constant wall thickness across the radially widening portion 163 as well as along the cylindrical portion 164. Consequently, the radially widening portion 163 features a beveled inside-facing portion 166a that merges or extends into an upper end face 166 that forms a lower, hence a distal end of the base portion 162. As illustrated in FIG. 9, the gas outlet 36 is arranged directly adjacent to the end face 166. A gas stream entering the inside portion of the deflector panel 161 in axial direction may be therefore redirected or deflected by the beveled portion 166a and may be directly guided into the adjacently-located gas outlet 36. In comparison to the embodiment as illustrated in FIG. 1, the axial distance (a) between the base portion 162 and the at least one gas outlet may vanish or may substantially equal zero.

Figure 11:
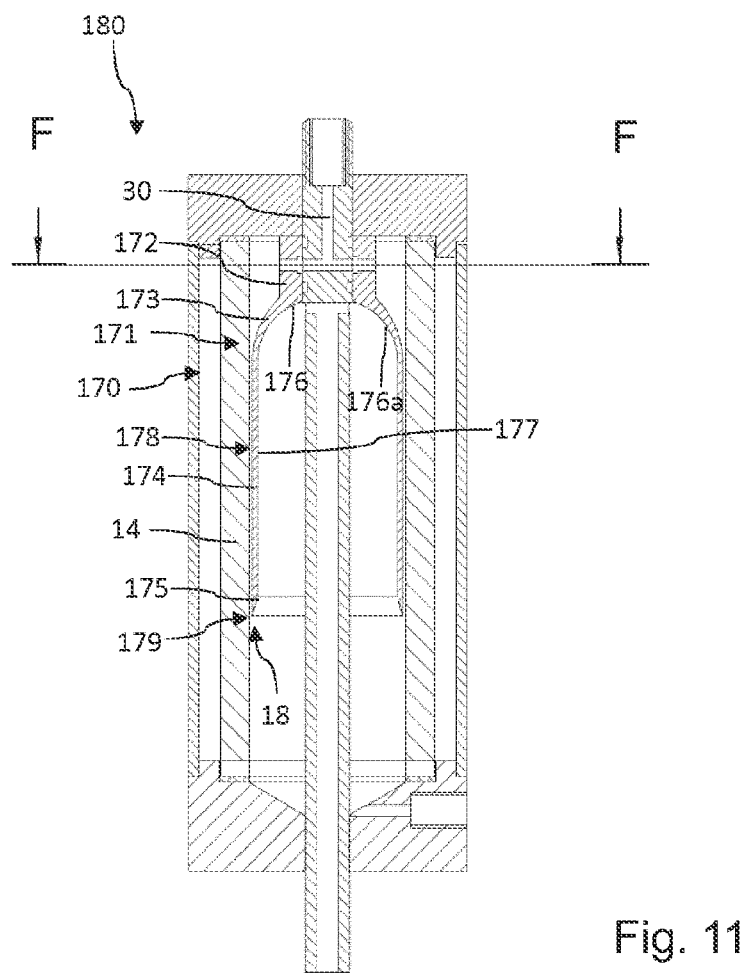
FIG. 11 shows a longitudinal cross section through another gas liquid separator.
Figure 12:
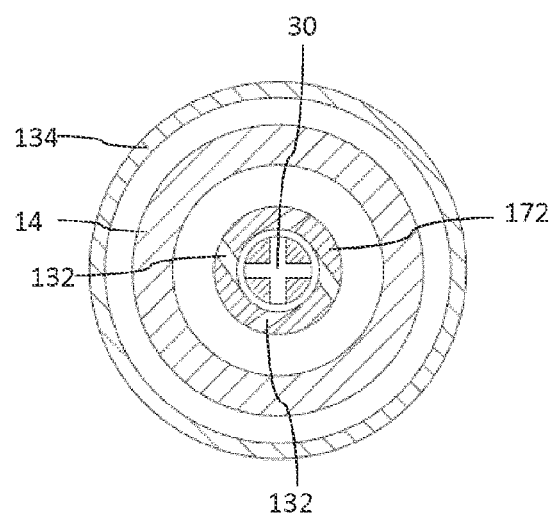
FIG. 12 shows a cross section along F-F of the gas liquid separator according to FIG. 11.

In FIGS. 11 and 12 a further embodiment of a gas liquid separator 180 is schematically illustrated. This gas liquid separator 180 is substantially identical to the gas liquid separators 150 or 130 except that the deflector 170 features a different shape and geometry. In comparison to the deflector 160 as shown in FIG. 9, the deflector 170 according to the embodiment of FIG. 11 also comprises a deflector panel 171 featuring a substantially cylindrically or sleeve-like-shaped base portion 172 integrally formed with a radially widening portion 173.

Also here, the radially widening portion 173 extends in distal direction into a radially widened cylindrical portion 174 that comprises a free edge 179 at a lower, hence at a distal free end. The cylindrical portion 174 features a tapered sidewall portion 175 at its lower free edge 179. In the same way as already described in connection with the embodiment according to FIG. 9, the cylindrical portion 174 forms an annular flow channel 178 with the surrounding sidewall 14 of the chamber 12.

In contrast to the gas liquid separator 150 shown in FIG. 9, the deflector panel 171 of the deflector 170 according to FIG. 11 features an arched or dome-shaped radially widening portion 173. As seen from the upper proximal end of the chamber the radially widening portion 173 features a convex shape and extends into the adjacently located cylindrical portion 174. Also here, an inside-facing wall section 177 of the deflector panel 171 corresponds to the outer shape or to the outer circumference of the deflector panel 171.

Consequently, the upper or proximal end face 176 of the deflector panel 171 extends into the plane-shaped or tubular-shaped inside-facing sidewall section 177 of the cylindrical portion 174 via a curved portion 177a. The curved portion 177a exhibits a concave shape and is configured to deflect and to redirect an upwardly- or proximally-directed stream of gas radially inwardly into the at least one gas outlet 36. Also here, and as already described in regard of FIG. 9, the at least one gas outlet 36 is located axially adjacent or flushes with the proximal end face 176 of the deflector panel 171.

Figure 13:
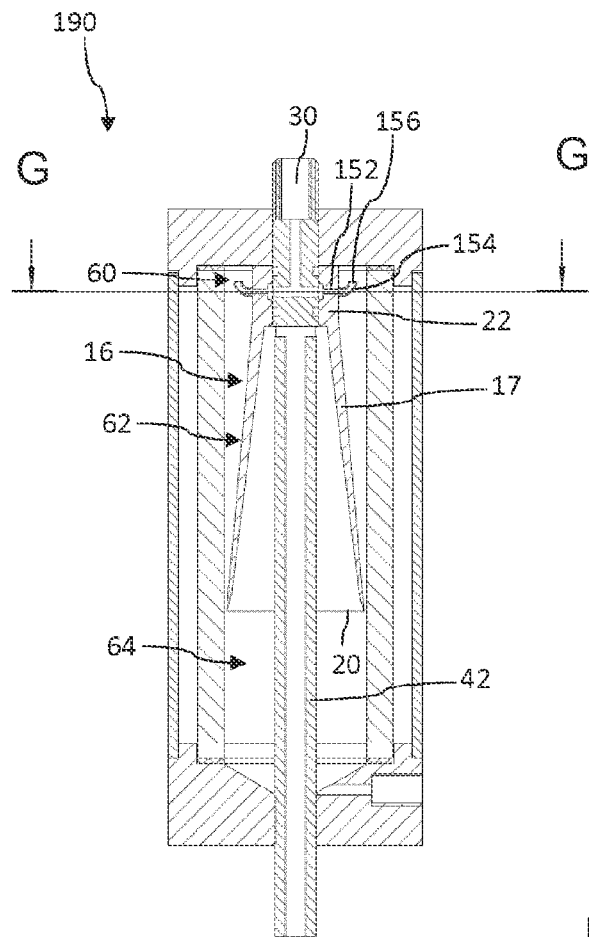
FIG. 13 shows another embodiment of a gas liquid separator in longitudinal cross section and FIG. 14 shows a cross-section along G-G of the gas liquid separator according to FIG. 13.
Figure 14:
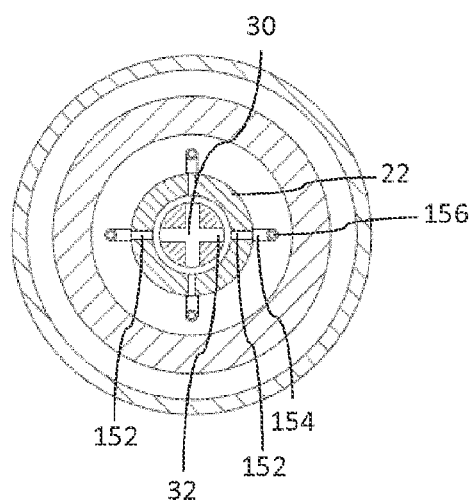

In FIGS. 13 and 14 another embodiment of a gas liquid separator 190 is shown featuring a structure that is substantially identical to the structure of the gas liquid separator 130 as shown in FIG. 6. The gas liquid separator 190 varies from the embodiment as shown in FIGS. 6 and 7 by its inlets 152 which radially-outwardly extend through the cylindrically-shaped base portion 22 of the deflector 16. Here, the inlets 152 comprise a curved section 154 extending into the inlet chamber portion 60.

Said curved sections 154 comprise a bending of about 90° so that a free end 156 of the curved sections 154 faces in a proximal direction, hence towards an inside face portion of the head section 44. In this way, the aerosol entering the chamber 12 via the inlet duct 30 and the various inlets 152 is redirected by about 180° and may therefore be injected into the chamber 12 in proximal direction.

Here, the aerosol may not only experience inertia- or impact-based separation by the curved section 154 of the inlets 152 but may also impinge on an inside-facing, hence a lower and inward-facing surface of the head section 44. In this way, not only the sidewall 14 but also the head section 44 may act as a deflector plate for supporting or for enhancing impact- or inertia-based gas liquid separation.

Even though the bended configuration of inlets 152 is only shown in connection with a cone-shaped deflector panel 17, said inlets 152 may be arbitrarily combined with other deflector panels 160, 170 as for instance shown in FIG. 9 or 11.

The invention claimed is:

1. A gas-liquid separator, comprising:

a chamber extending in an axial direction (z) and having at least a flow chamber portion extending into a collection chamber portion, a deflector arranged in the flow chamber portion, the deflector having a deflector panel extending radially outwardly (r) and in axial direction (z) to form a narrowing flow channel between the deflector and a side wall of the chamber, wherein the deflector panel has a free edge, at least one gas outlet shielded by the deflector panel and being arranged axially offset from the free edge, and an inlet duct extending into the chamber in axial direction (z), wherein the inlet duct branches off into a plurality of radially extending inlets at a proximal end of the chamber.

2. The gas-liquid separator according to claim 1, wherein the deflector panel is substantially cone shaped.

3. The gas-liquid separator according to claim 1, wherein the deflector panel comprises a radially outwardly extending widening portion and a cylindrical portion extending axially adjacent to the widening portion.

4. The gas-liquid separator according to claim 1, wherein the free edge of the deflector panel forms an annular flow gap with the side wall of the cylindrically shaped chamber.

5. The gas-liquid separator according to claim 1, wherein the at least one gas outlet is in flow connection with an axially extending gas outlet duct.

6. The gas-liquid separator according to claim 5, wherein the deflector comprises a closed base portion integrally formed with a proximal portion of the deflector panel to form a cup-shaped deflector.

7. The gas-liquid separator according to claim 5, wherein the deflector is arranged on a proximal end portion of the gas outlet duct.

8. The gas-liquid separator according to claim 1, further comprising a liquid collecting portion at a distal end being in fluid connection with a liquid outlet duct.

9. The gas-liquid separator according to claim 1, further comprising a partition member arranged upstream of the deflector and extending over the cross-section of the chamber for separating the flow chamber portion from an inlet chamber portion arranged upstream thereof.

10. The gas-liquid separator according claim 9, wherein the partition member comprises at least one axial through opening at an outer radial edge to form an axial passage adjacent to the side wall of the chamber.

11. The gas-liquid separator according to claim 10, wherein the at least one through opening extends at a predefined angle ($\alpha$) with respect to the axial direction (z).

12. The gas-liquid separator according to claim 1, wherein the inlet duct is radially centrally arranged inside the chamber and is further in fluid connection with at least one inlet facing or extending radially outwardly towards the side wall of the chamber.

13. The gas-liquid separator according to claim 1, wherein the at least one inlet comprises a curved section extending into the inlet chamber portion or flow chamber portion and facing in a proximal direction with a free end.

14. An chromatography system comprising:

at least one reservoir for at least one of storing or preparing at least one solvent mixture, a chromatography column, at least one detection or analyzing unit, and at least one gas-liquid separator according to claim 1.

15. The chromatography apparatus according to claim 14, designed as supercritical fluid chromatography (SFC) apparatus, wherein the gas-liquid separator is operable to separate CO2 and Methanol.

16. A conversion kit to convert a high-performance liquid chromatography (HPLC)-type chromatography system into a SFC-type chromatography system, the kit comprising at least a gas-liquid separator according to claim 1 configured to replace a gas-liquid separator of the HPLC-type chromatography system.

* * * * *